United States Patent [19]

Bertram et al.

[11] Patent Number: 6,153,770
[45] Date of Patent: Nov. 28, 2000

[54] FURFURYLTHIOALKANES, A PROCESS FOR THEIR PREPARATION AND THEIR USE

[75] Inventors: Heinz-Jürgen Bertram, Teterboro, N.J.; Peter Werkhoff, Höxter; Matthias Güntert, Holzminden, both of Germany

[73] Assignee: Haarmann & Reimer, Holzminden, Germany

[21] Appl. No.: 08/870,352

[22] Filed: Jun. 5, 1997

[30] Foreign Application Priority Data

Jun. 7, 1996 [DE] Germany ............................ 196 22 745

[51] Int. Cl.⁷ ............................ C07D 307/41; A23L 1/22
[52] U.S. Cl. ............................ 549/498; 426/535
[58] Field of Search ............................ 549/498; 514/461; 426/535

[56] References Cited

U.S. PATENT DOCUMENTS

| | | | |
|---|---|---|---|
| 3,702,253 | 11/1972 | Winter et al. | 549/472 |
| 3,900,581 | 8/1975 | Winter et al. | 426/535 |
| 3,900,582 | 8/1975 | Winter et al. | 426/535 |
| 3,931,246 | 1/1976 | Winter et al. | 549/472 |
| 3,943,260 | 3/1976 | Winter et al. | 426/535 |
| 3,952,024 | 4/1976 | Winter, et al. | 549/498 |
| 3,952,026 | 4/1976 | Winter et al. | 549/472 |
| 3,989,713 | 11/1976 | Winter et al. | 548/517 |
| 4,092,334 | 5/1978 | Mookherjee et al. | 204/286 |

*Primary Examiner*—Alan L. Rotman
*Attorney, Agent, or Firm*—Joseph C. Gil; Noland J. Cheung

[57] ABSTRACT

The invention relates to new furfurylthioalkanes of the formula

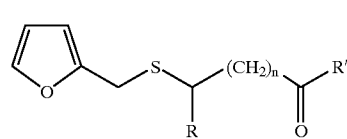

(I)

wherein n can be zero or 1

R represents the methyl or ethyl radical if n is 0, and represents hydrogen or the methyl radical if n is 1, and R' represents methyl or ethyl, a process for their preparation and their use as aroma substances.

2 Claims, No Drawings

FURFURYLTHIOALKANES, A PROCESS FOR THEIR PREPARATION AND THEIR USE

The invention relates to new furfurylthioalkanes, a process for their preparation and their use as aroma substances.

It has been found that selected furfurylthioalkanes have valuable organoleptic properties.

The invention relates to compounds of the formula

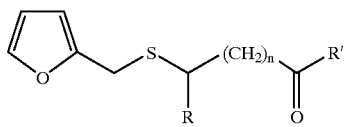

(I)

wherein
n can be zero or 1,
R represents the methyl or ethyl radical if n is 0, and represents hydrogen or the methyl radical if n is 1, and
R' represents methyl or ethyl.

Preferred compounds I correspond to the formulae

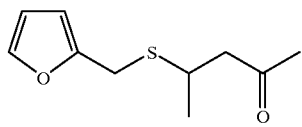

(Ia)

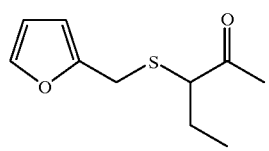

(Ib)

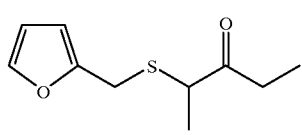

(Ic)

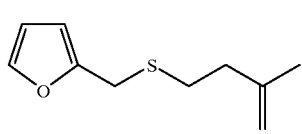

(Id)

The compounds I can be prepared by reaction of furfurylmercaptan with keto compounds.

The invention therefore furthermore relates to a process for the preparation of the compounds I by reaction of furfurylmercaptan with ketones of the formulae

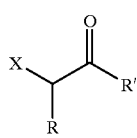

(II)

wherein
x represents halogen, preferably chlorine or bromine, and
R represents methyl or ethyl, or

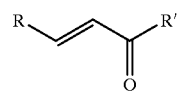

(III)

wherein R represents hydrogen or methyl, where R' in each case has the abovementioned meaning.

Preferred ketones II are, for example, 3-chlorobutan-2-one, 3-bromobutan-2-one, 3-chloropentan-2-one and 3-bromopentan-2-one, and preferred ketones III are, for example, but-3-en-2-one and pent-3-en-2-one.

The process can be carried out in bulk, but preferably in inert organic solvents. Preferred organic solvents include alcohols, such as ethanol, and ethers, such as ethyl tert-butyl ether and tetrahydrofuran.

The reaction of furfurylmercaptan with ketone II is carried out in the presence of a base in order to bind the hydrogen halide liberated. It is preferable to employ at least equivalent amounts of the base. The reaction of furfurylmercaptan with ketone III can be catalyzed by addition of a base. While equivalent amounts often also leads to the best results here, very small amounts may very often also be sufficient; the optimum amount can easily be determined by a few experiments.

Preferred bases include, for example, amines, such as triethylamine, morpholine, piperidine and pyridine, alcoholates, such as sodium methylate and potassium tertbutylate, and hydroxides, such as sodium hydroxide and potassium hydroxide.

The process can be carried out within a wide temperature range. Temperatures from −30 to +50, in particular from 0 to 30° C., are in general preferred.

The compounds (I) according to the invention are valuable aroma substances; they are distinguished by very low taste threshold values. Thus, a test panel of 20 testers in a triangular test using 4-furylthiobutan-2-one in 0.5% strength by weight aqueous sodium chloride solution even found a significant difference between the blank sample and the sodium chloride solution comprising only one ppb of 4-[(2-furylmethyl)thio]-2-butanone. For 4-[(2-furylmethyl)thio]-2-pentanone, a test panel of 6 trained testers found a significant difference between the 0.5% strength by weight sodium chloride solution and the 0.5% strength by weight sodium chloride solution comprising 1.5 ppb of 4-[(2-furylmethyl)thio]-2-pentanone.

The descriptions of taste for the individual compounds of the formula (I) according to the invention when used in 0.5% strength by weight aqueous sodium chloride solution are:

4-[(2-furylmethyl)thio]-2-butanone:
when added in an amount of 1 ppb: burnt, oniony, coffee note, roasted, mocha, sulphurous 4-Furfurylthio-pentan-2-one:
when added in an amount of 1 ppb: coffee, mocha, roasted 4-[(2-furylmethyl)thio]-3-pentanone
when added in an amount of 0.6 ppb: coffee, roasted, delicate bitter chocolate, mocha 4-[(2-furylmethyl)thio]-3-butanone:

when added in an amount of 150 ppb: roasted, sulphurous, coffee, mild mocha

With their specific taste in the direction of mocha, the compounds (I) according to the invention have the effect of intensifying and rounding off the taste in coffee and mocha compositions. However, the compounds according to the invention also have the effect of rounding off the aroma and increasing the fullness of taste in other aroma compositions, for example nut aromas.

The aroma compositions prepared using the compounds according to the invention can be employed in the entire food and luxury goods sector and in animal feeds. They are particularly suitable for fat compositions, baked goods, extruded products, ready-made meals, meat and sausage products, soups, sauces, preserved vegetables and all types of industrially produced animal feed.

The new furfuryl-thioalkanes according to the invention are as a rule used in amounts of 5 ppt to 1% by weight, preferably 100 ppt to 100 ppm, based on the ready-to-eat food.

The invention thus furthermore relates to the use of the compounds I as aroma substances.

The percentage data in the following examples are percentages by weight.

EXAMPLES

Example 1

4-[(2-furylmethyl)thio-2-pentanone 10 g of furfurylmercaptan and 15 g of 3-penten-2-one were dissolved in 100 ml of ethanol. The solution was stirred at room temperature for 48 hours. The solvent was then distilled off in vacuo at 50° C. The residue (18 g) was purified by preparative high pressure liquid chromatography (HPLC). 9 g of 4-[(furylmethyl)thio]-2-pentanone (purity 95%) were obtained. The IR, NMR and mass spectra of the compound agree with the structure described for it.

IR Spectrum (film):

| Wave number [cm$^{-1}$] | |
| --- | --- |
| 745.2 | m |
| 935.3 | m |
| 1010.9 | m |
| 1159.9 | m |
| 1361.9 | m |
| 1420.7 | m |
| 1504.5 | m |
| 1711.5 | s |
| 2925.6 | w |
| 2966.8 | m |

(Intensity of the IR bands: w = weak, m = moderate, s = strong)

Example 2

4-Furfurylthio-butan-2-one was obtained analogously to Example 1 using 3-buten-2-one instead of 3-penten-2-one.

Example 3

3-Furylthio-pentan-2-one 11.2 g of potassium tert-butylate, dissolved in 100 ml of dry tetrahydrofuran, are initially introduced into the reaction vessel at room temperature. 11.4 g of furfurylmercaptan are added dropwise at 20° C. When the addition is complete, the mixture is subsequently stirred for a further 30 minutes. 16.5 g of 3-bromopentan-2-one are then added dropwise in the course of 30 minutes and the mixture is subsequently stirred for one hour. For working up, the mixture is poured onto 100 ml of water and extracted twice with diethyl ether, and the combined organic phases are washed with water, dried over sodium sulphate and concentrated. 19 g of crude product (purity 84.1%) are obtained. For further purification, the product is subjected to bulb tube distillation. 10 g of 3-furfurylthio-pentan-2-one, which has a purity of 97.5%, are obtained. The IR, NMR and mass spectra of the compound agree with the structure described for it.

IR Spectrum (film):

| Wave number [cm$^{-1}$] | |
| --- | --- |
| 747.1 | m |
| 936.6 | m |
| 1010.8 | m |
| 1153.2 | m |
| 1213.9 | w |
| 1355.7 | m |
| 1417.6 | w |
| 1504 | m |
| 1695.4 | s |
| 2967.4 | m |

Example 4

3-Furfurylthio-butan-2-one was obtained analogously to Example 3 using 3-bromobutan-2-one instead of 3-bromopentan-2-one.

Example 5

2-Furfurylthio-3-pentanone was obtained analogously to Example 3 using 2-bromopentan-3-one instead of 3-bromopentan-2-one.

IR Spectrum (film):

| Wave number [cm$^{-1}$] | |
| --- | --- |
| 746.3 | m |
| 936.6 | m |
| 1011.4 | m |
| 1152.6 | m |
| 1353.2 | m |
| 1455.1 | m |
| 1504.1 | m |
| 1696.1 | s |
| 2936.3 | m |
| 2975.1 | m |

Use.

A coffee composition was prepared by mixing the following constituents in the stated parts by weight:

|  | Parts by weight |
| --- | --- |
| 3,5(6)-Dimethyl-2-ethylpyrazine | 20 |
| Diacetyl | 20 |
| Isobutyraldehyde | 20 |
| 3-Methyl-2-cyclopentan-2-ol-1-one | 50 |
| 2,6-Dimethoxyphenol | 50 |
| Caproic acid | 100 |
| 2,5-Dimethyl-4-hydroxyfuran-3(2H)-one | 30 |
| Furfurylthioalkane according to the invention | 10–100 |
| Triacetin | 610–700 |
|  | 1000 |

Patent claims:
1. A compound of the formula

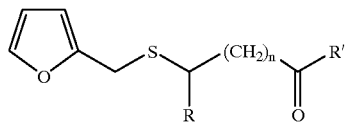
(I)

wherein
  n can be zero or 1,
  R represents the methyl or ethyl radical if n is 0, and represents the methyl radical if n is 1, and
  R' represents methyl or ethyl.
2. A compound according to claim 1, selected from the group consisting of
  3-[(2-furylmethyl)thio]-2-pentanone,
  4-[(2-furylmethyl)thio]-2-pentanone,
  4-[(2-furylmethyl)thio]-2-butanone and
  4-[(2-furylmethyl)thio]-3-pentanone.

* * * * *